United States Patent [19]
Barath et al.

[11] Patent Number: 5,242,397
[45] Date of Patent: * Sep. 7, 1993

[54] CATHETER DEVICE AND METHOD OF USE FOR INTRAMURAL DELIVERY OF PROTEIN KINASE C AND TYROSINE PROTEIN KINASE INHIBITORS TO PREVENT RESTENOSIS AFTER BALLOON ANGIOPLASTY

[75] Inventors: Peter Barath, West Hollywood, Calif.; Ferenc Denes, Budapest, Hungary

[73] Assignee: Cedars-Sinai Medical Center, Los Angeles, Calif.

[*] Notice: The portion of the term of this patent subsequent to May 12, 2009 has been disclaimed.

[21] Appl. No.: 821,232

[22] Filed: Jan. 2, 1992

Related U.S. Application Data

[63] Continuation-in-part of Ser. No. 598,405, Oct. 16, 1990, Pat. No. 5,112,305, and a continuation-in-part of Ser. No. 472,898, Jan. 31, 1990, abandoned.

[51] Int. Cl.$^5$ ............................................ A61M 29/00
[52] U.S. Cl. ...................................... 604/96; 604/101
[58] Field of Search ............................ 604/96, 51–53, 604/265, 266, 99, 101, 97, 104

[56] References Cited

U.S. PATENT DOCUMENTS

| | | | |
|---|---|---|---|
| 4,689,041 | 10/1985 | Corday et al. | |
| 4,710,469 | 12/1987 | Liang et al. | 435/194 |
| 4,801,452 | 1/1989 | Hunter et al. | 424/94 |
| 4,968,307 | 4/1989 | Dake et al. | |
| 4,994,072 | 8/1989 | Bhate et al. | |
| 5,002,531 | 6/1987 | Bonzel | |
| 5,017,370 | 5/1990 | Hunter et al. | |
| 5,021,044 | 1/1989 | Sharkawy | |
| 5,112,305 | 5/1992 | Barath | 604/101 |
| 5,128,321 | 2/1992 | Murray et al. | 514/12 |

FOREIGN PATENT DOCUMENTS

WO89/05148 6/1989 World Int. Prop. O.
WO89/12478 12/1989 World Int. Prop. O.

OTHER PUBLICATIONS

Dusing, R. et al. "Mechanisms and Significance of Arteriolar Media Thickening in Arterial Hypertension" (abstract only) *Klin Wochenschr* 66/23: 1151–1159, 1988.

Sauro, M. D. et al. "Prolactin Induces Proliferation of Vascular Smooth Muscle Cells Through a PKC-Dependent Mechanism" *Journal of Cellular Physiology* 148: 133–138, 1991 (abstract only).

Pauletto, P. et al., "Changes in Myoglobin, Creatine Kinase and Creatine Kinase-MB After Percutaneous Transluminal Coronary Angioplasty for Stable Angina Pectoris," *Am. Jnl. Cardiology*, 59(9):999–1000 (1987).

Okamura, T. et al., "Combined Treatment of Coenzyme $Q_{10}$ and Aprotinin with Intraaortic Balloon Pumping following Aorto-Coronary Bypass Surgery," *Jpn. Jnl. Surg.*, 14(2):97–103 (1984).

Barath, P. et al., "Low Dose of Antitumor Agents Prevents Smooth Muscle Cell Proliferation After Endothelial Injury," *JACC*, 13(2):252A (Feb. 1989).

Uehara, Y. et al., "Inhibition of Transforming Activity of Tyrosine Kinase Oncogenes by Herbimycin A," *Virology*, 164:294–98 (1988).

Hagiwara, M. et al., "Differential Effects of Flavonoids as Inhibitors of Tyrosine Protein Kinases and Serine-/Threonine Protein Kinases," *Biochem. Pharm.*, 37(15):2987–92 (1988).

Hoffman, J. et al., "Enhancement of the Antiproliferative Effect of cis-Diamminedichloroplatinum (II) and Nitrogen Mustard by Inhibitors of Protein Kinase C," *Int. J. Cancer*, 42:382–88 (1988).

Nishizuka, Y., "The Molecular Heterogeneity of Protein Kinase C and its Implications for Cellular Regulation," *Nature*, 334:661–65 (Aug. 1988).

*Primary Examiner*—C. Fred Rosenbaum
*Assistant Examiner*—Chalin Smith
*Attorney, Agent, or Firm*—Lyon & Lyon

[57] ABSTRACT

The present invention discloses a method of treatment of an atherosclerotic blood vessel. Protein kinase C and tyrosine protein kinase inhibitors are delivered by means of a specialized catheter system to the deeper layers of the vessel wall with only minimal interruption of the vessel endothelium. This system will allow high local concentrations of otherwise toxic agents directly at the site of an atherosclerotic plaque to prevent and/or reduce the incidence of late restenosis attributed to cellular hyperplasia or rethrombosis.

12 Claims, 6 Drawing Sheets

CATHETER DEVICE AND METHOD OF USE FOR INTRAMURAL DELIVERY OF PROTEIN KINASE C AND TYROSINE PROTEIN KINASE INHIBITORS TO PREVENT RESTENOSIS AFTER BALLOON ANGIOPLASTY

This application is a continuation in part of both application Ser. No. 472,898 filed Jan. 31, 1990, now abandoned, and U.S. Pat. No. 5,112,305, Ser. No. 598,405, filed Oct. 16, 1990 and allowed May 12, 1992.

This invention relates generally to the medical and veterinary medical field of atherosclerotic lesion treatment. More particularly, this invention relates to a catheter device and a method for the local delivery into the vessel wall of specific inhibitors of protein kinase C (PKC) and tyrosine protein kinase (TPK) following balloon angioplasty, to prevent restenosis precipitated by either reoccurrence of the initial thrombotic lesion or by hyperplasia of the local vessel cellular components.

BACKGROUND OF THE INVENTION

Atherosclerotic Cardiovascular Disease (ASCVD) is the most common cause of death in industrial countries (*JAR*, 150:1263-1269 (1988)). Peripheral Vascular Disease (PVD) also contributes to the morbidity and mortality rates in these populations. In both diseases, damage is mediated by an occlusive lesion of the involved vessel. This lesion is generically called a thrombus. A thrombus is an aggregate of elements formed on the wall of an involved vessel from constituents of the blood in response to a thrombogenic stimuli. This process of thrombus formation is termed thrombosis. Body tissues distal to the occlusion are deprived of their normal blood flow and its ensuing benefits.

Over the years various medical interventions have been employed to remove or otherwise treat an offending thrombotic lesion. Various surgical methods have also been used resulting in significant medical advancement. The surgical interventions include replacement of the aorta, and coronary artery by-pass grafting (CABG), the gold standard for treatment of lesions involving the coronary vessels of the heart. However, despite these procedures and their advancement in the treatment of this disease, a need continues to exist for treatment with less expensive and less invasive methods.

Percutaneous transluminal angioplasty (PTA). or balloon angioplasty, has proven to be a useful non-surgical procedure for the treatment of localized occlusive atherosclerotic lesions of both coronary and peripheral vessels (Merck Manual, 15th Ed., p. 559). This technique involves the cannulation of an affected vessel with a special catheter. An uninflated balloon portion of the catheter is introduced into the narrowed vessel lumen so that it is juxtapositioned to the lattice-like network of the forming thrombus. Inflation of the balloon portion of the catheter compresses the offending thrombus against the vessel wall thereby restoring lumen patency. The balloon is then typically deflated and the catheter is withdrawn.

Following PTA, blood flow through the artery is usually significantly improved. Unfortunately, however, although more than 90% of the balloon dilations are initially successful, there is a high rate (35-40%) of late restenosis. Longer balloon inflation times, high doses of calcium-channel blockers, steroids, and other drug regimens have been attempted but so far have proved unsuccessful in combating this problem (*NEJM*, 316:701 (1987)). Indeed, about one-third of all patients treated with PTA return for a second or third procedure, thus reducing the long-term benefits of the procedure (*Eur. Heart J.*, 9:31-37 (1988)). A need exists therefore, for a method to increase the long-term benefits of PTA, with the aim of preventing restenosis of the diseased vessel.

Vessels of the human body are lined by a smooth surface known as the endothelium. The innermost layer of the endothelium is called the intima. This impervious layer improves vascular bloodflow hemodynamics and shields deeper vessel wall layers from contact with the blood itself. Unfortunately, successful PTA invariably involves some interruption of this lining with a resulting violation of the barrier it provides between the deeper placed smooth muscle cells (SMC) of the vessel wall and the blood itself. Local hemodynamic flow characteristics are also affected. It is some combination of these two factors that leads to a later recurrence of partial vessel occlusion in 35-40% of otherwise successful PTA procedures.

With regard to the SMC, one mechanism of vessel restenosis is SMC hyperplasia. In histologic sequences that resemble tumor growth, the vessel SMCs dedifferentiate from a contractile to a synthetic phenotype, followed by intense proliferation and the production of connective tissue. In an attempt to prevent this cell proliferation and post-angioplasty restenosis, we reported the systemic administration of antitumor cytostatic agents which would selectively damage active and proliferating smooth muscle cells (*JACC* 13(2):252A (1989)). Systemically administered drugs such as anticoagulants and vasodilators have so far proven ineffective to prevent restenosis. More radical treatment involving agents such as cytostatic drugs or general enzyme blockers may prevent smooth muscle cell proliferation but often these agents are toxic to humans at the levels necessary to effectively block development of the involved pathology. As with many systemically administered drugs, the chief complication is the adverse effects or toxicities on normal cells. For that reason, the inventors have proposed local administration of such agents. In particular, cytotoxic antitumor agents are suggested as a means of selectively damaging the hyperplastic SMCs.

Problems remain, however, in the exact method by which this local administration should be accomplished. The conventional methods of drug therapy, including tablets, capsules, slow-release formulations and injectables, all result in typical fluctuations of drug concentrations at the target site. With every dose of the drug, serum concentrations may alternatively reach levels that produce adverse side effects and then decline to values significantly less than therapeutic. As a result, in order to be effective, potent agents destined to treat specific sites must travel through the bloodstream in much larger concentrations than those required at the target (*Med. Res. Rev.*, 1(4):373-386 (1981)). Even with local administration of these agents, the normal blood flow of the vessel will dilute the local concentration of the therapeutic agent by a wash-out effect. A need exists therefore, for a method of preventing restenosis that assures adequate therapeutic effect while reducing or eliminating toxic side effects. A need also exists for a system whereby otherwise toxic therapeutic agents are concentrated and localized within the affected vessel wall segment. The present invention satisfies these needs and provides related advantages as well.

SUMMARY OF THE INVENTION

The present invention provides a novel catheter system and a method of preventing restenosis after balloon angioplasty which avoids the cited disadvantages of prior art methods of balloon angioplasty and drug administration.

As noted above, the anatomical substrate of restenosis following balloon angioplasty is a tumor-like proliferation of smooth muscle cells in the vessel wall referred to as intimal hyperplasia. It has been demonstrated that this cell proliferation is initiated and stimulated by a large number of growth factors, (proto) oncogenes, and cytokines, which act through either protein kinase C (PKC) or tyrosine protein kinase (TPK). Inhibition of PKC and TPK by local delivery into the vessel wall of specific inhibitors prevents smooth muscle cell proliferation and thereby prevents balloon catheter induced restenosis.

The catheter system of the present invention will deliver the specific PKC and TPK inhibitor agents intramurally at the precise vessel segment that is diseased but without allowing the agents to diffuse distally into the bloodstream. One embodiment of the present invention employs a double lumen catheter that has additional tubular extensions or studs projecting at various angles from the outer surface of the outermost lumen. By abruptly increasing the pressure in the outer lumen, the tubular extensions deliver the PKC and TPK inhibitor agents to locations deep within the vessel wall. Another embodiment of the invention would allow blood flow to continue distally while absorption occurred more slowly within particular alternating arcs of the vessel lumen. The PKC and TPK inhibitor agents could be bound to macromolecules to enhance their ability to avoid washout from the vessel wall, if this were desired and feasible.

A more comprehensive understanding of the present invention will be evident after reviewing the forthcoming diagrammatic representations with their detailed description.

BRIEF DESCRIPTION OF THE DRAWINGS

The present invention will be described in connection with the accompanying figures in which:

In FIG. 4, the delivery system is shown in the insertion phase.

FIG. 5 shows the delivery system in the inflated phase.

FIG. 6 shows the delivery system in the bursting phase.

INDEX OF FIGURE LABELS

Figure 1:
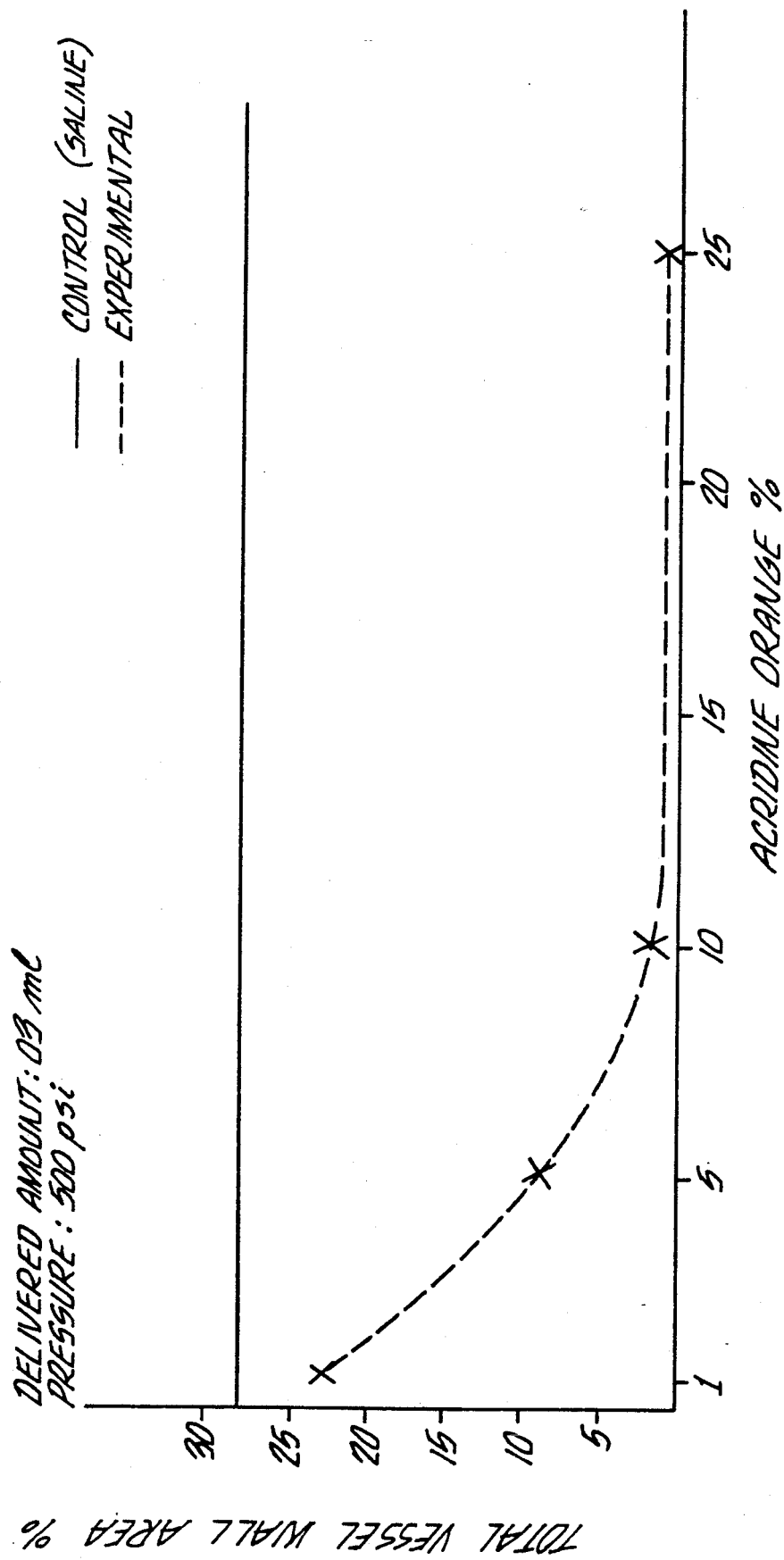
FIG. 1 is a graph showing the effect of the TPK inhibitor agent, acridine orange, on the proliferation of smooth muscle cells 14 days after balloon angioplasty. The percentage of proliferated area to total vessel area is shown for the control vessel (saline) in the solid line compared to a vessel receiving various concentrations of inhibitor in the broken line.

1. Balloon surface;
2. Catheter shaft;
3. Luer connector of the catheter shaft;
4. Central lumen;
5. Luer connector of the central lumen;
6. Tapered tip of the catheter;
7. Tapered shaft of the catheter;
8. Slide holes on the shaft;
9. Radiopaque platinum marker;
10. Tubular extension;
11. Lumen of the tubular extension;
12. Extension-free (occluding) area of the balloon;
13. Adventitia;
14. Vessel wall;
15. Endothelial surface of the vessel;
16. Fluid; and
17. Fluid burst into the vessel wall.

DETAILED DESCRIPTION OF THE INVENTION

A series of compounds which act as inhibitors of reactions involved in growth factor signal transduction have been studied with a view to their potential use in tumor chemotherapy. (Int. J. Cancer, 42:382–388 (1988)). We have unexpectedly discovered that the use of some of these compounds was effective in preventing or inhibiting restenosis after balloon angioplasty.

Following angioplasty, the smooth muscle cells in the vessel wall begin to proliferate as a result of initiation and stimulation by a large number of growth factors (including PDGF, IGF, EGF, TGF), (proto) oncogenes (including fos, ras, src), and cytokines (including IL-1 and TNF). All of these factors act through either protein kinase C (PKC) or tyrosine protein kinase (TPK). Suitable pharmaceutical agents effective in this invention therefore include any inhibitor of PKC or TPK.

One such TPK inhibitor, the antibiotic herbimycin A, has been shown to reverse the morphologies of chicken and mammalian cells that have been transformed by some tyrosine protein kinase oncogenes (Virology, 164:294–298 (1988)). In addition, to confirm inhibition of transforming activity of tyrosine kinase oncogenes by herbimycin, a drastic reduction in kinase activities was demonstrated in the transformed cells.

ST 638 and bioflavonoids, like quercetin, have also been shown to inhibit the growth and proliferation of certain malignant cells in vivo and in vitro by inhibition of several protein kinases including tyrosine kinase. Further, isoquinolinesulfonamides such as H-7 and H-8 potently inhibited protein kinase C (*Biochemical Pharmacology*, 37:2987-2992 (1988)). Other inhibitors of protein kinase C include the phorbol ester TPA as well as tamoxifen, staurosporine (*Int. J. Cancer*, 42:382-388 (1988)), acridine derivatives, chlorpromazine and dibucaine (phospholipid interacting drugs).

Before local delivery of these inhibitors to the vessel wall, their effectiveness may be facilitated by first binding the inhibitors to other molecules such as heparin to form macromolecules. This will result in the inhibitor remaining in the vessel wall for a sufficient time to enable their inhibitory action. Production of the macromolecule-bound form of these inhibitors may be achieved by any method known in the art.

By way of example, the PKC or TPK inhibitors are delivered to the vessel wall by means of a catheter and an inflatable balloon perforated with holes. The catheter, having this inflatable balloon on the distal end, is passed through the patient's venous system to the diseased section of the vessel. A fluid containing an effective dose of the macromolecule-bound inhibitor is directed through the catheter, through the holes in the inflated balloon, and to the diseased vessel wall. The inhibitor is allowed to contact the vessel wall for a period which allows sufficient action by the inhibitor. The dosage and period of action will depend upon the inhibitor employed. The balloon is then deflated and the catheter withdrawn.

EXAMPLE 1

A coronary angioplasty balloon catheter was inserted into both the left (control) and right (experimental) iliac arteries of rabbits. Balloon dilation was performed three times at +25% and 7 atm. Immediately following the dilation procedure, 0.3 ml normal saline with 3 mg Pulmonite (albumin as binder) was delivered into the left artery (control) at 500 psi and a rate of 1 ml/sec. Similarly, 0.3 ml of aqueous acridine orange solution of various concentrations (1, 5, 10, 25%) bound to Pulmonite was delivered into the right artery at 500 psi and a rate of 1 ml/sec.

Fourteen days after the above procedure, the rabbits were sacrificed for histological examination. Measurement of the area of intimal hyperplasia as a percentage of the total vascular wall area was measured using computer assisted planimetry. The results are shown in the graph. It can be observed that balloon angioplasty induces the formation of a proliferative area of cells that reaches 28% of the total vessel wall area in those arteries treated only by normal saline and the pulmonite carrier. Acridine orange on the other hand, dramatically decreased this area of cell proliferation and at a 10% concentration almost completely prevents the proliferation.

EXAMPLE 2

Figure 2A:
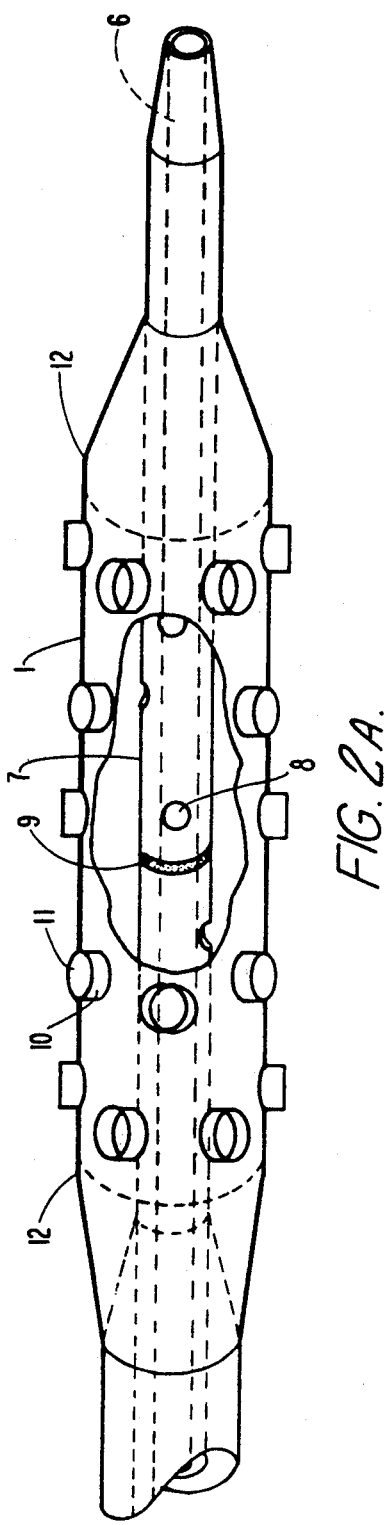
FIG. 2A is a longitudinal section of the inflated balloon (1), the catheter shaft (2) and the central lumen (4). The catheter ends in a tapered luminal tip (6). The central lumen (4) is to accommodate a steerable guide wire or to inject contrast material. The catheter shaft (2) is tapered into the shaft of the balloon (7) which is perforated by several sideholes (8) and has a radiopaque platinum marker (9). From the balloon surface (1) tubular extensions (10) with lumen (11) stick out. The two ends of the balloon (12) are free of extensions and serve to isolate the area where fluid is burst into the vessel wall from the other parts of the vessel lumen.
Figure 2B:
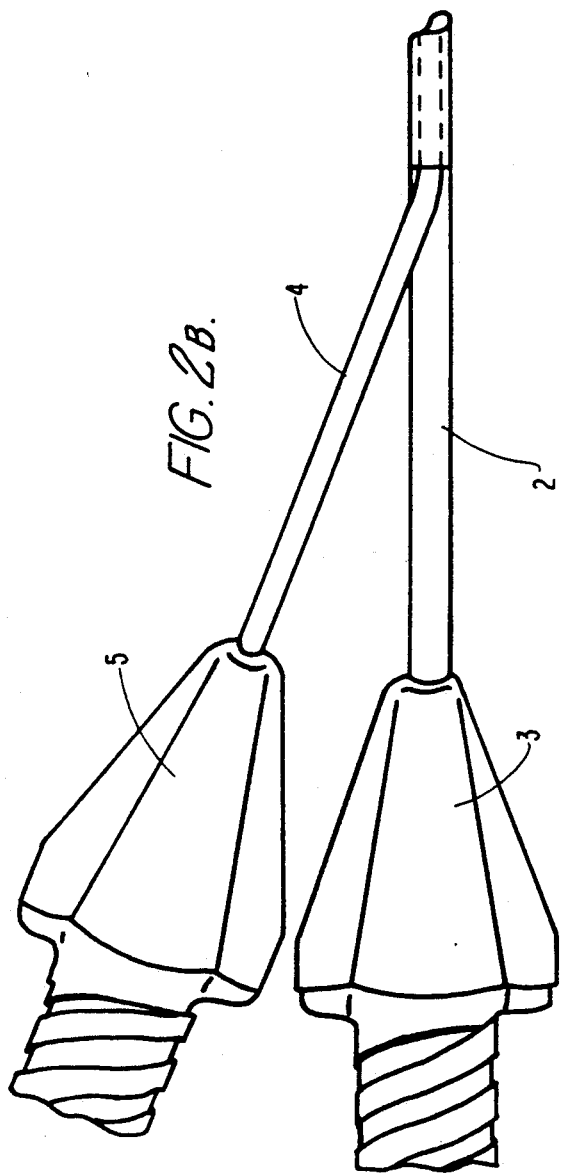
FIG. 2B illustrates the Luer connector (3) for the catheter shaft (2) and the Luer connector (5) for the central lumen (4).
Figure 3:
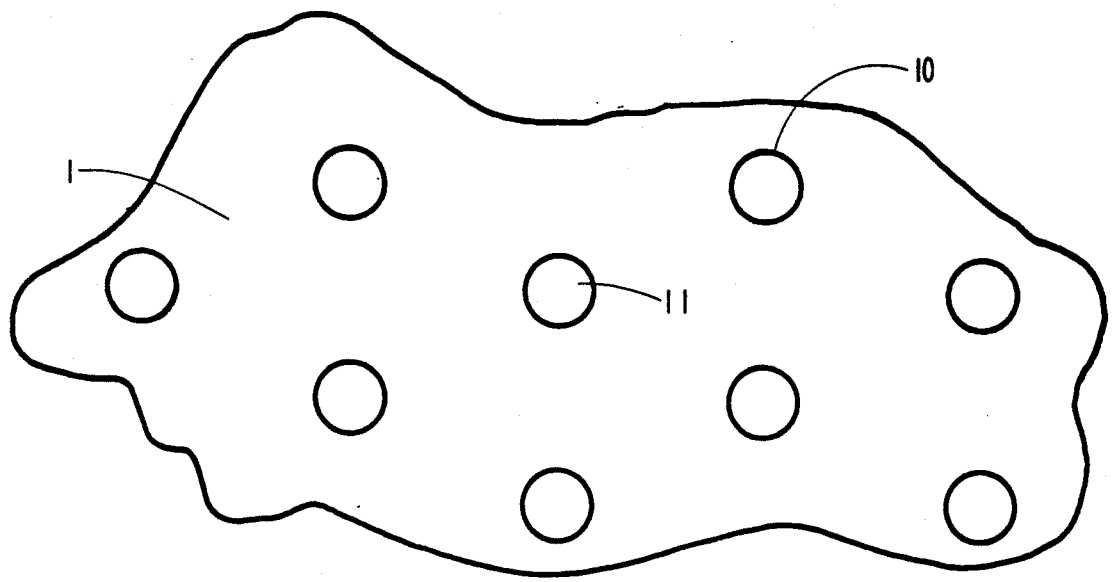
FIG. 3 shows the balloon surface (1) with the tubular extensions (10) and with their holes (11). While the size of the catheter and the balloon is determined by vessel size, the diameter (a) and the length (b) of the tubular extensions (10) are about 0.50 mm and 0.25 mm, respectively.
Figure 4:
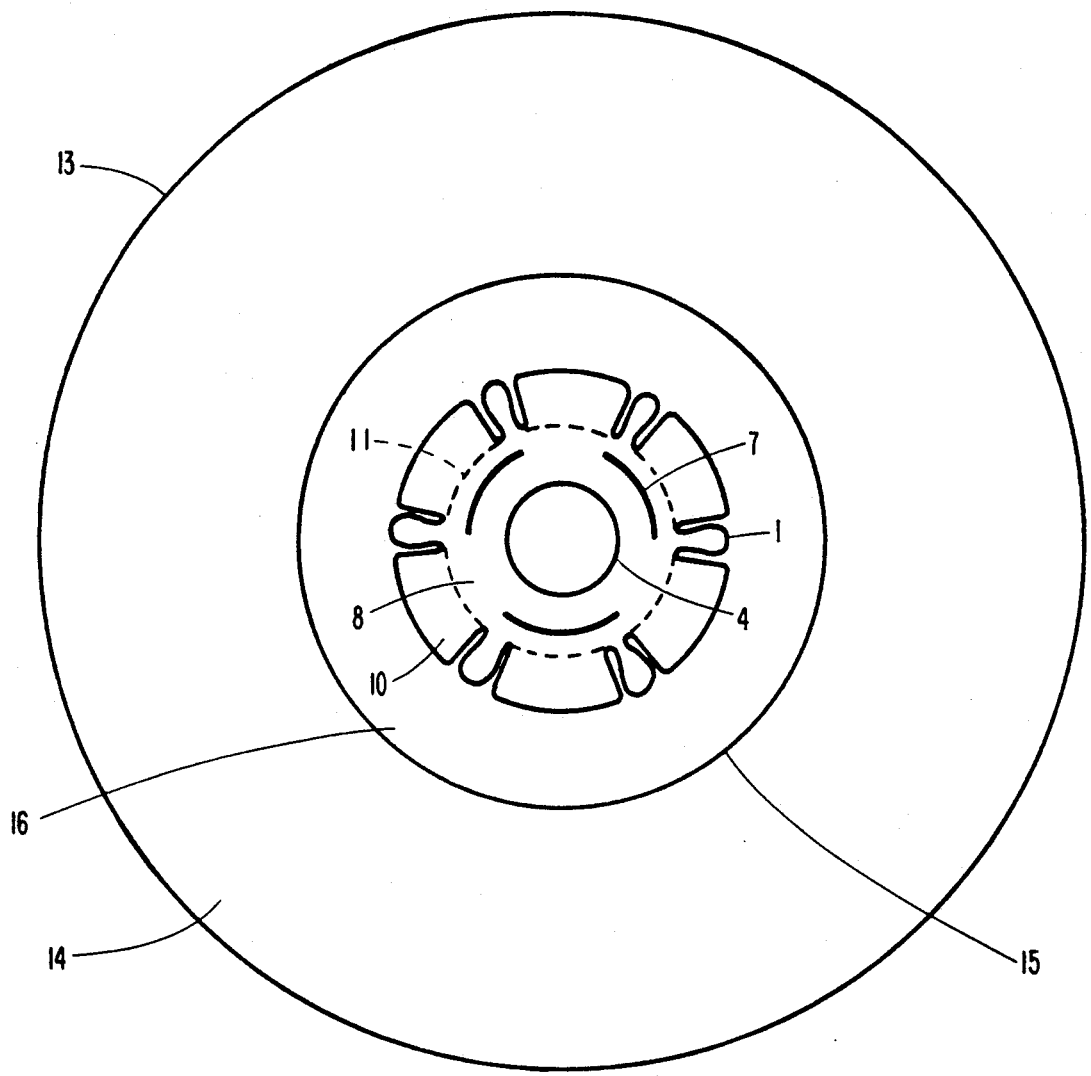
FIGS. 4 through 6 demonstrate the use of the delivery system.
Figure 5:
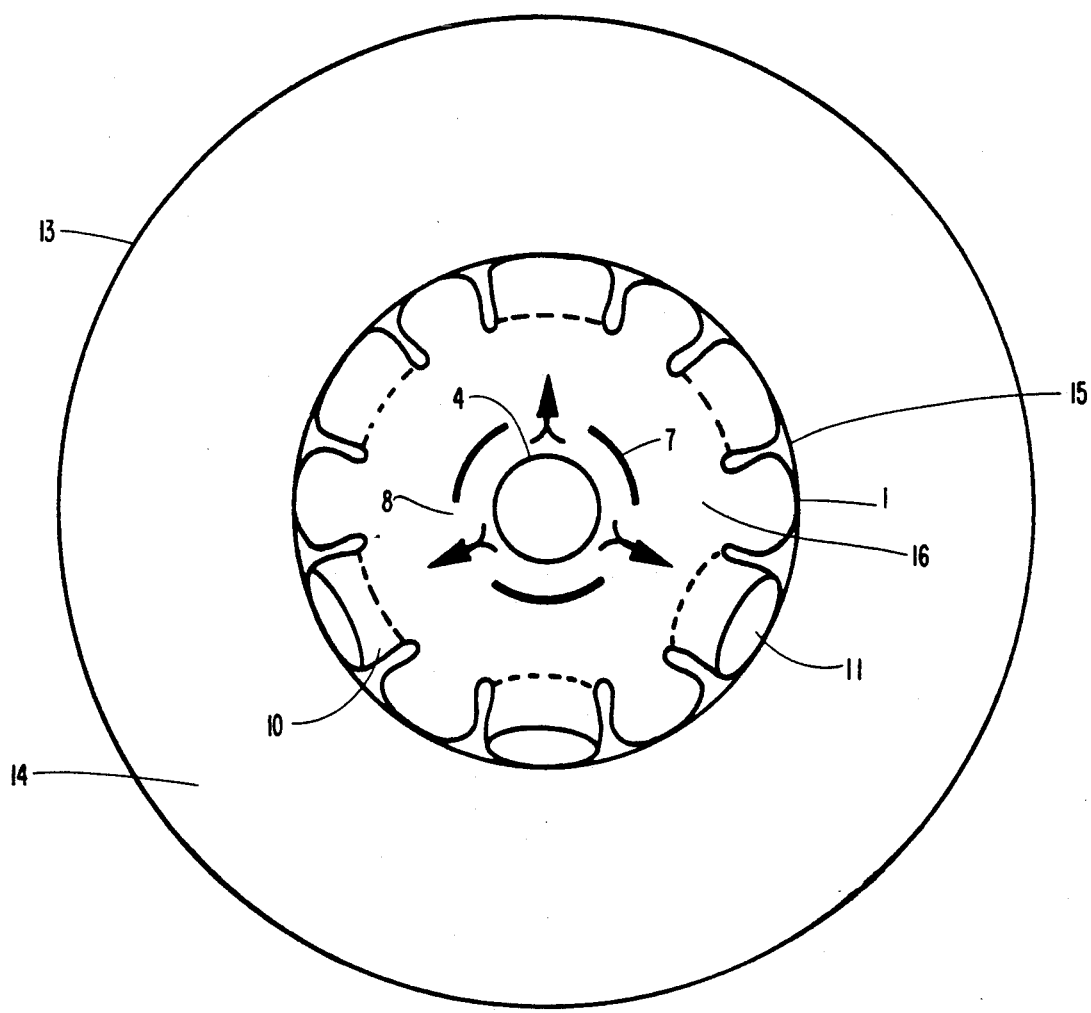

The catheter of the present invention was inserted into the vessel segment which had undergone angioplasty, over a guide wire in a deflated state (FIG. 4). The drawing shows the adventitial (13), endothelial (15) surfaces of the vessel, the vessel wall (14) and the vessel lumen. The tubular extensions (10) of the balloon (11) were inverted when the balloon was deflated (insertion phase). After appropriate positioning of the balloon within the desired vascular segment, the catheter was connected to an angiographic injector through the Luer connector of the catheter shaft (3 on FIG. 2B). The pressure in the balloon was slowly built up by injection of a solution of a PKC or TPK inhibitor agent at a low flow rate to the point when the balloon surface (1) closely leaned against the endothelial surface of the vessel (15). At this point the tubular extensions (10) were not penetrating into the vessel wall (FIG. 5, inflation phase), and the fluid was hardly leaking through the lumen of the extensions (11).

Figure 6:
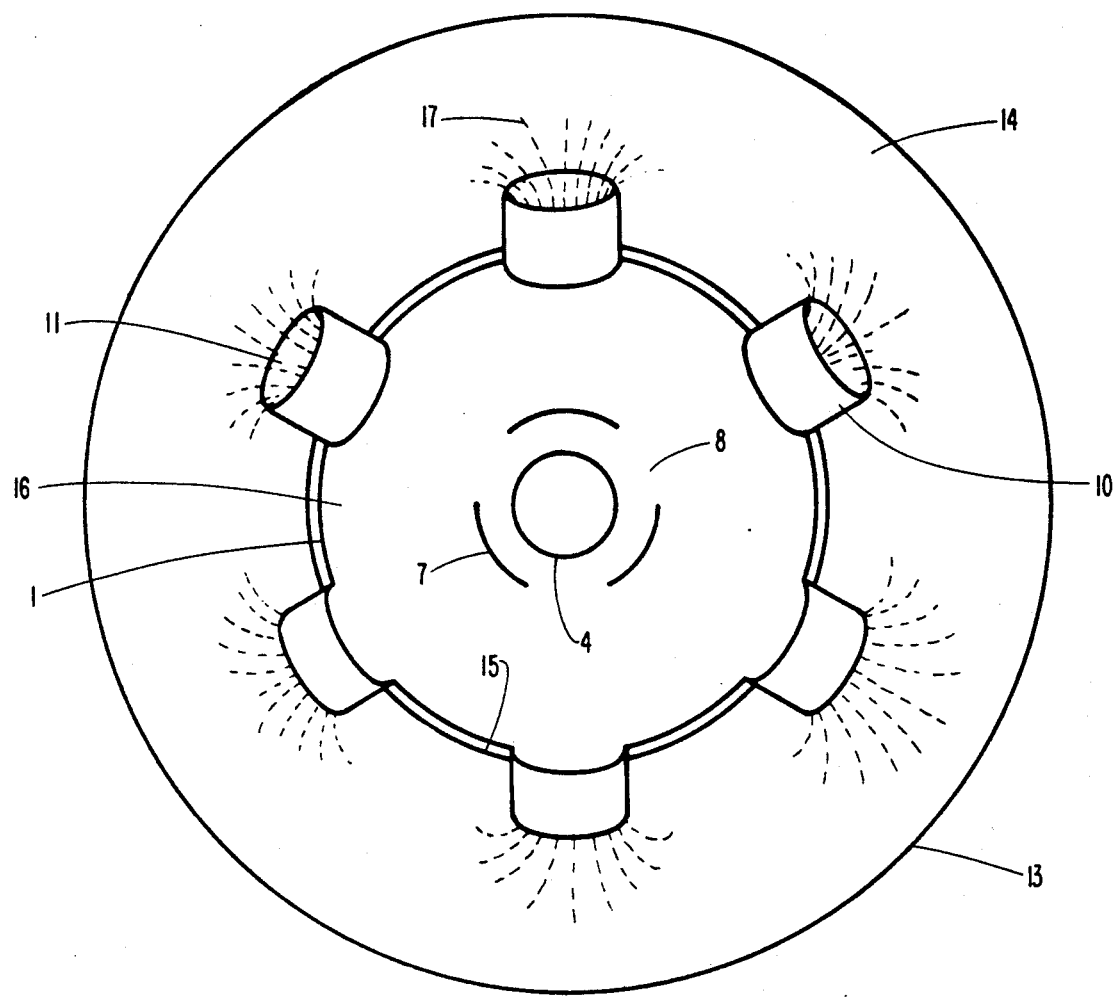

The flow rate and the pressure was abruptly increased in the balloon by injection of a small volume (0.25 ml-0.50 ml) from the injector (FIG. 6, bursting phase) causing the tubular extensions (10) to suddenly penetrate into the vessel wall (15) where the fluid (17) was propelled into the deeper layers of the wall (15) through the holes of the extensions (11).

After 10 seconds, the balloon was deflated and removed from the vessel.

Although specific delivery procedures and PKC and TPK inhibitors are described above, the invention is not intended to be limited solely as described. The foregoing detailed description is given for clearness of understanding only. No unnecessary limitations are to be understood or inferred therefrom, as modifications are readily apparent to those skilled in the art from the description and are believed within the scope of the invention.

We claim:

1. A method of treating a blood vessel which contains an atherosclerotic lesion whereby a protein kinase C inhibitor agent is delivered into the vessel wall at or near the site of the atherosclerotic lesion comprising:

insertion of a catheter device system into a diseased blood vessel, the catheter being one which contains an inflatable balloon studded with hollow tubular extensions that communicate between the outer surface of the balloon and the inner lumen of the catheter device system;

slow filling of the catheter balloon so that the balloon surface's tubular extensions abut the inner vessel wall; and rapid infusion of a bolus of a protein kinase C inhibitor agent sufficient to effect bursting of the vessel's endothelium by the tubular extensions and delivery of the protein kinase C inhibitor agent to the deeper layers of the vessel wall through the extensions.

2. The method of claim 1 wherein the protein kinase C inhibitor agent is selected from the group consisting of H-7, H-8, TPA, tamoxifen, staurosporine, acridine derivatives, chlorpromazine and dibucaine.

3. The method of claim 2 wherein the protein kinase C inhibitor agent is bound to a macromolecule.

4. A method of treating a blood vessel which contains an atherosclerotic lesion whereby a tyrosine protein kinase inhibitor agent is delivered into the vessel wall at or near the site of the atherosclerotic lesion comprising:

insertion of a catheter device system into a diseased blood vessel, the catheter being one which contains an inflatable balloon studded with hollow tubular extensions that communicate between the outer surface of the balloon and the inner lumen of the catheter device system;

slow filling of the catheter balloon so that the balloon surface's tubular extensions abut the inner vessel wall; and rapid infusion of a bolus of a tyrosine protein kinase inhibitor agent sufficient to effect bursting of the vessel's endothelium by the tubular extensions and delivery of a the tyrosine protein kinase inhibitor agent to the deeper layers of the vessel wall through the extensions.

5. The method of claim 4 wherein the tyrosine protein kinase inhibitor agent is selected from the group consisting of herbimycin, ST 638, bioflavonoids and quercetin.

6. The method of claim 5 wherein the tyrosine protein kinase inhibitor agent is bound to a macromolecule.

7. A catheter device and system useful in the treatment of a blood vessel which contains an atherosclerotic lesion, said catheter comprising:

a centrally hollow shaft having proximal and distal ends, said central portion comprising a first longitudinally extending lumen with an opening on its proximal end adapted to receive a protein kinase C inhibitor agent or a guide wire, and a second longitudinally extending lumen circumferentially disposed around and capable of communicating with the first longitudinally extending lumen and with a similarly adapted proximal end;

a plurality of inflatable balloon type regions longitudinally and circumferentially disposed along the axis of said second longitudinally extending lumen and capable of communication with the protein kinase C inhibitor agent;

a plurality of radially extending hollow tubular studs disposed along said inflatable regions extending outwardly from said catheter device and capable of communication with the protein kinase C inhibitor agent directly to either or both of the inner lumens.

8. The catheter device of claim 7 wherein the protein kinase C inhibitor agent received by the catheter is selected from the group consisting of H-7, H-8, TPA, tamoxifen, staurosporine, acridine derivatives, chlorpromazine and dibucaine.

9. The catheter device of claim 8 wherein the protein kinase C inhibitor agent is bound to a macromolecule.

10. A catheter device and system useful in the treatment of a blood vessel which contains an atherosclerotic lesion, said catheter comprising:

a centrally hollow shaft having proximal and distal ends, said central portion comprising a first longitudinally extending lumen with an opening on its proximal end adapted to receive a tyrosine protein kinase inhibitor agent or a guide wire, and a second longitudinally extending lumen circumferentially disposed around and capable of communicating with the first longitudinally extending lumen and with a similarly adapted proximal end;

a plurality of inflatable balloon type regions longitudinally and circumferentially disposed along the axis of said second longitudinally extending lumen and capable of communication with the tyrosine protein kinase inhibitor agent;

a plurality of radially extending hollow tubular studs disposed along said inflatable regions extending outwardly from said catheter device and capable of communication with the tyrosine protein kinase inhibitor agent directly to either or both of the inner lumens.

11. The catheter device of claim 10 wherein the tyrosine protein kinase inhibitor agent received by the catheter is selected from the group consisting of herbimycin, ST 638, bioflavonoids and quercetin.

12. The catheter device of claim 11 wherein the tyrosine protein kinase inhibitor agent is bound to a macromolecule.

* * * * *

UNITED STATES PATENT AND TRADEMARK OFFICE
CERTIFICATE OF CORRECTION

PATENT NO. : 5,242,397
DATED : September 7, 1993
INVENTOR(S) : Peter Barath, et. al.

It is certified that error appears in the above-indentified patent and that said Letters Patent is hereby corrected as shown below:

Column 1, line 26, change "JAR" to read --AJR--.

line 48, change "." to read --,--.

Column 3, line 50, change "." to read --,--.

Signed and Sealed this

Twenty-sixth Day of April, 1994

Attest:

BRUCE LEHMAN

*Attesting Officer*      *Commissioner of Patents and Trademarks*